United States Patent [19]
Juni

[11] Patent Number: 6,120,792
[45] Date of Patent: Sep. 19, 2000

[54] MEDICATED SKIN PATCH AND METHOD FOR ITS USE

[76] Inventor: Jack E. Juni, 25595 York, Royal Oak, Mich. 48067

[21] Appl. No.: 09/069,362

[22] Filed: Apr. 29, 1998

[51] Int. Cl.[7] .................................................. A61K 9/70
[52] U.S. Cl. ....................... 424/448; 424/447; 424/443; 424/449; 514/887
[58] Field of Search ............................. 602/57; 424/447, 424/448, 446, 449

[56] References Cited

U.S. PATENT DOCUMENTS

| | | | |
|---|---|---|---|
| D. 363,126 | 10/1995 | Dusek | D24/189 |
| 3,565,075 | 2/1971 | Jerry | 128/268 |
| 4,117,841 | 10/1978 | Perrotta et al. | 128/155 |
| 4,192,299 | 3/1980 | Sabatano | 128/155 |
| 4,812,305 | 3/1989 | Vocal | 424/448 |
| 4,858,604 | 8/1989 | Konishi | 128/156 |
| 4,899,739 | 2/1990 | Konishi | 128/156 |
| 5,061,258 | 10/1991 | Martz | 604/307 |
| 5,181,914 | 1/1993 | Zook | 604/307 |
| 5,330,452 | 7/1994 | Zook | 604/307 |
| 5,415,866 | 5/1995 | Zook | 424/448 |
| 5,536,263 | 7/1996 | Rolf et al. | 604/307 |
| 5,593,395 | 1/1997 | Martz | 604/304 |
| 5,662,925 | 9/1997 | Ebert et al. | 424/447 |
| 5,722,943 | 3/1998 | Sessions | 602/57 |

*Primary Examiner*—Thurman K. Page
*Assistant Examiner*—R. Bawa
*Attorney, Agent, or Firm*—Gifford, Krass, Groh, Sprinkle, Anderson & Citkowski, P.C.

[57] ABSTRACT

A medicated skin patch for delivering a topical anesthetic to an irritated region of skin includes a bibulous pad for contacting and covering the irritated region. A topical anesthetic is imbibed in the bibulous pad. A sheet of thin material covers the pad and projects beyond the pad to form an attachment region. At least a portion of the attachment region has an adhesive coating for affixing the sheet to the skin so that the pad is held in contact with the irritated region.

22 Claims, 2 Drawing Sheets

MEDICATED SKIN PATCH AND METHOD FOR ITS USE

FIELD OF THE INVENTION

This invention relates generally to topical medicating devices and more specifically to a medicated adhesive patch for delivering a topical anesthetic.

BACKGROUND OF THE INVENTION

Both children and adults often develop some type of skin irritation from a variety of causes including insect bites, plant irritations, contact dermatitis and minor injuries. Persons encountering this situation typically wish to avoid the itching or pain associated with the irritation, and want to encourage the irritation to heal. It is often also desirable to cover the irritated area to prevent further irritation or inadvertent scratching. Ideally, an anesthetic, a medical compound that desensitizes tissue, would provide relief from both itching and pain associated with a skin irritation. However, the use of topical lotions and creams designed for itch and pain relief is generally ineffective. This is primarily due to poor or slow penetration of the active ingredients of the cream or lotion into the skin. The active ingredients contained in the skin creams and lotions are typically not in a form which easily penetrates the skin; and as a consequence, they have less than desired medical effect and evaporate or are rubbed or rinsed from the skin.

Therefore, there is a need for a topical anesthetic delivery system which is capable of delivering a topical anesthetic in a penetrating form to an irritated region of skin and further capable of maintaining the topical anesthetic in contact with the skin for an extended period so that therapeutically effective amounts of the anesthetic may penetrate the skin.

SUMMARY OF THE INVENTION

There is disclosed herein a medicated skin patch for delivering a topical anesthetic to a region of skin which has been irritated. The medicated skin patch includes a bibulous pad for contacting and covering the irritated region of skin. A topical anesthetic is imbibed in the bibulous pad. A sheet of thin impermeable material covers the pad and projects beyond the pad to form an attachment region. At least a portion of the attachment region has an adhesive coating for affixing the sheet to the skin so that the bibulous pad is held in contact with the irritated region of skin.

In some embodiments, the topical anesthetic is in a gelled or otherwise thickened matrix. Some other embodiments of the present invention also include a topical antiseptic, a topical antibiotic, an anti-inflammatory, an antihistamine, and/or a moisturizer imbibed in the bibulous pad. Yet other embodiments of the medicated skin patch include a release layer for covering the pad and adhesive layer. The release layer is configured to be removed from the patch prior to affixing the patch to the skin.

DETAILED DESCRIPTION OF THE PREFERRED EMBODIMENT

Figure 1:
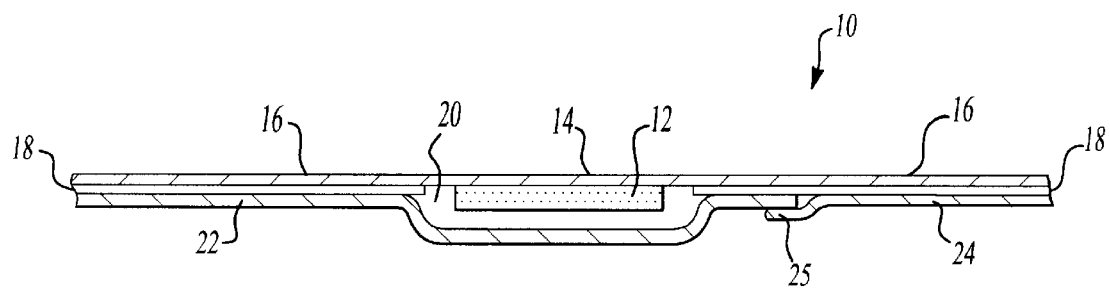
FIG. 1 is a cross-sectional side view of a medicated skin patch according to the present invention.
Figure 2:
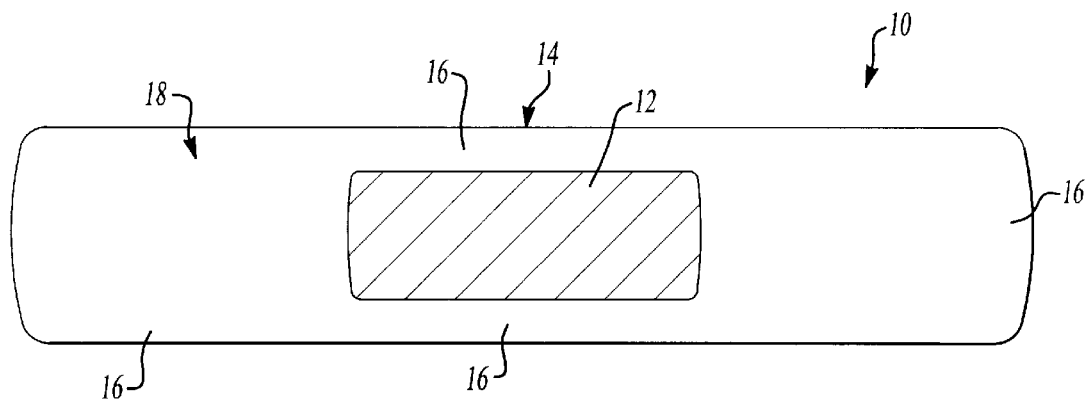
FIG. 2 is a bottom view of a medicated skin patch according to the present invention.

Referring now to FIGS. 1 and 2, a medicated skin patch according to the present invention is generally shown at 10. The medicated skin patch 10 includes a bibulous pad 12 which is designed to contact and cover a region of skin which has been irritated. The bibulous pad 12 may be made of various materials which are capable of absorbing and holding a liquid or gel. Some preferred materials include cotton wool, woven textiles, nonwoven textiles, paper pulp and polymeric foams, most preferably hydrophilic polymer foams. Imbibed in the pad 12 is a topical anesthetic, which is defined herein as a medicinal compound that desensitizes tissue. The anesthetic preferably is designed for topical use and is in a gelled or otherwise thickened matrix. The medicated skin patch 10 also includes a sheet of thin impermeable material 14 which covers the pad 12 and projects beyond the pad 12 to define an attachment region.

In the embodiment shown, the sheet 14 is an elongated rectangle with the generally rectangular pad 12 centered on and affixed to the sheet 14. The attachment region includes those portions of the sheet 14 which extend lengthwise beyond the pad 12 as well as those portions of the sheet 14 which project beyond the sides of the pad 12. The attachment region of the sheet 14 is generally indicated in the figures as 16. At least a portion of the attachment region 16 has an adhesive coating 18 for affixing the sheet 14 to the skin so that the pad 12 is held in contact with the irritated region. The adhesive coating 18 is located on the same side of the sheet 14 as the pad 12; the side designed to contact the skin. Preferably, the entire attachment region 16 is coated with adhesive 18 so that the sheet 14 is securely affixed to the skin and the pad 12 is surrounded by the affixed sheet 14.

As stated earlier, the pad 12 is preferably affixed to the sheet 14. This is to ease application of the medicated skin patch 10 to the skin and to prevent the pad 12 from moving relative to the sheet 14. One preferred method of forming the medicated skin patch 10 is to first coat the entire sheet 14 with adhesive 18 and then to place the pad 12 onto the sheet 14. In this way the adhesive 18 holds the pad 12 to the sheet 14 as well as affixes the sheet 14 to the skin.

As shown in FIG. 1, the medicated skin patch may also include an optional pad cover 20. The cover 20 covers the side of the pad 12 which is not affixed to the sheet 14. The cover 20 may serve one or more purposes. First, it may serve to help retain the thickened anesthetic in the pad 12. Secondly, it will allow the topical anesthetic to pass from the pad 12 through to the irritated region. In this context, the covering 20 may act to control the rate of passage of the gelled anesthetic to the skin so that the rate of penetration into the skin is controlled. The cover 20 may also act to prevent the pad 12 from sticking to the skin. The cover 20 may be of various materials as will be clear to one of ordinary skill in the art. One possible material is a porous or microporous polymer sheet with fluorinated polymers being particularly preferred.

Also shown in FIG. 1 is an optional release layer which is formed of two pieces 22 and 24. The release layer covers the pad 12 and the adhesive layer 18 during shipping and storage to prevent the adhesive layer 18 from sticking to the wrong surface and to help retain the anesthetic in the bibulous pad 12 and prevent evaporation. As is known in the art, such release layers are typically fabricated from a sheet of paper, textile, or polymer having a low adhesion coating of silicone, fluoropolymer, or the like disposed thereupon. When a person wishes to use the medicated skin patch 10, they first remove the pieces of the release layer 22 and 24 thereby exposing the pad 12 and adhesive layer 18. The bibulous pad 12 is then placed over an irritated region of skin and adhesive layer 18 is allowed to contact the surrounding skin thereby retaining the pad 12 in position. As shown in FIG. 1, the release layer pieces 22 and 24 preferably overlap to form an overlapping portion 25. This overlapping portion 25 makes it easier for a user to grip the pieces 22 and 24 of the release layer and remove them. Preferably, the overlapping portion 25 is adjacent to the attachment region 16 of the thin material 14 rather than the pad 12. This improves the seal over the pad 12 further preventing loss of medication.

The anesthetic imbibed in the bibulous pad 12 may be of several types. Preferably it is an anesthetic designed for topical application. Numerous such anesthetics will be apparent to one of ordinary skill in the art. One preferred embodiment contains benzocaine as the active ingredient. The anesthetic may be thickened or made viscous in one of several ways. It is preferred that the anesthetic is thickened by gelling. Presence of the gelled or otherwise thickened matrix facilitates contact of the topical anesthetic with the skin, thereby enhancing its effect. A concentration of 10% benzocaine disposed in a gelled matrix is available commercially, and is typically used to alleviate teething pain in infants. This material may be advantageously utilized in the present invention. Other topical anesthetics such as lidocaine, procaine, xylocaine and the like may be similarly employed, with or without a thickened matrix, and in various therapeutically effective concentrations.

The pad 12 may also imbibe other materials along with the thickened anesthetic. For example, a topical antibiotic, a topical antiseptic, an antiinflammatory, an antihistamine, and/or a moisturizer may be imbibed in the pad 12. A topical antiseptic and/or antibiotic would help to prevent infection. Some preferred topical antiseptics include iodine containing complexes, nitrofurazones, phenolic materials and mercury or silver containing materials. Alternatively, the topical antiseptic may be any other type as known to one of ordinary skill in the art. An antiinflammatory such as aspirin or ibuprofen will reduce swelling or inflammation. An antihistamine such as benadryl or an anti-irritant such as calamine will reduce allergic reactions. A moisturizer will serve to help soften the skin and to reduce irritation. Many moisturizers are possible as will be known to one of ordinary skill in the art. Examples include but are not limited to aloe, lanolin, glycerin, mineral oil, and the like.

The bibulous pad may also have a counter-irritant substance such as menthol imbibed into it to provide an immediate sensation of warmth when the patch 10 is applied. This will provide minor itch relief and contribute to the sense that the patch is working to relieve the irritation. Other materials which can be used to provide a similar feeling of warmth include capsaicin, clove oil and other aromatics.

The sheet 14 of thin material may be a polymer sheet. This preferred material is generally impermeable to moisture so as to prevent wetting of the pad 12 from the outside. The polymer sheet 14 also helps to prevent the gelled anesthetic from being transported through the sheet 14. The polymer sheet also serves to hold the moisture and heat of the skin below the patch 10 thereby creating a high humidity, high temperature microenvironment which causes skin pores to open and facilitates diffusion of the anesthetic into the skin. The higher concentration of medication in the thickened matrix as compared to the skin creates a concentration gradient of the medication. Because the concentration of medication is lower in the skin, the medication diffuses from the highly concentrated thickened matrix into the skin. By preventing the anesthetic from transporting through the sheet 14, the patch 10 also holds the anesthetic in contact with the skin for an extended period of time so that relief from pain and itch lasts for an extended period. The bibulous pad 12, in cooperation with the impermeable sheet 14, also acts as a reservoir for the anesthetic so that anesthetic continues to be available for penetration into the skin. The portion of the anesthetic that penetrates the skin is replaced by the supply available from the pad reservoir. This maintains the medicine concentration gradient and therefore the transportion of medication from the reservoir into the skin. It is desirable to allow the skin surrounding the irritated region, which is covered by the attachment region 16 of the patch 10, to breathe normally. Therefore, in one preferred alternative, the attachment region 16 polymer sheet is perforated so that moisture from the skin adjacent the attachment region can penetrate the material. The sheet of thin material 14 may also alternatively be a woven material to allow the sheet 14 to flex and conform to the skin. If the woven material is moisture permeable, the portion of the material which covers the pad 12 should preferably be backed with a moisture impermeable barrier to retain the anesthetic and to create the moist and warm microenvironment. The thin sheet of material 14 also serves the purpose of protecting the irritated region to prevent scratching or further injury.

Figure 3:
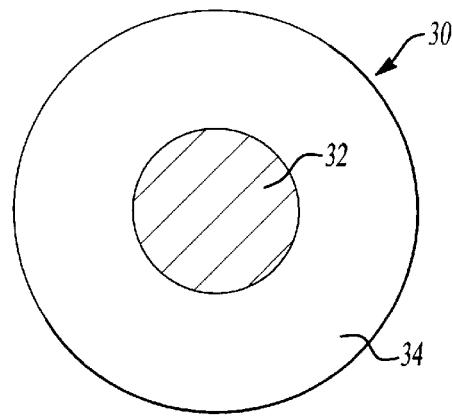
FIG. 3 is a bottom view of a first preferred alternative embodiment of a medicated skin patch according to the present invention.

Referring now to FIG. 3, a first preferred alternative embodiment of the medicated skin patch is generally shown at 30. This embodiment differs from the embodiment shown in FIGS. 1 and 2 in that the pad 32 and the sheet of thin material 34 are both round rather than rectangular. This embodiment is particularly convenient for small insect bites which typically create small round regions of irritation. The patch 30 is small and therefore less visible when applied to the irritated region.

Figure 4:
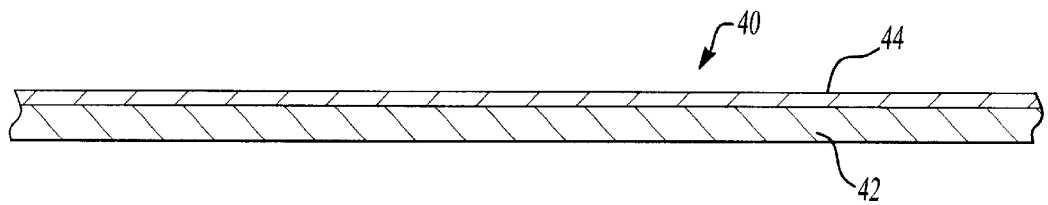
FIG. 4 is a cross-sectional side view of a medicated sheet according to the present invention.
Figure 5:
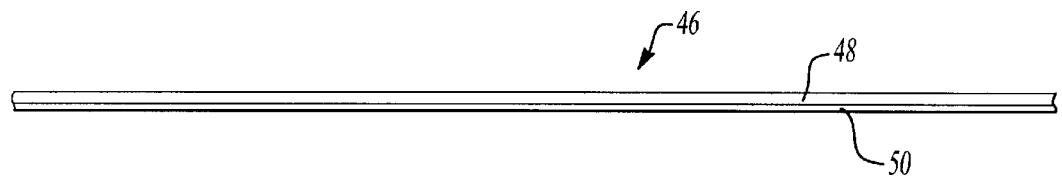
FIG. 5 is a cross-sectional side view of an adhesive sheet according to the present invention.
Figure 6:
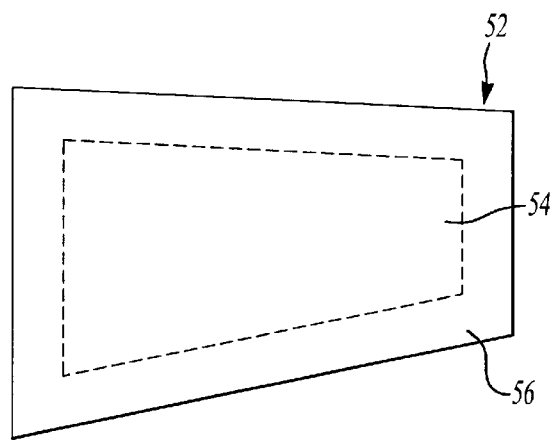
FIG. 6 is a top view of a piece of the medicated sheet of FIG. 4 covered by a piece of the adhesive sheet of FIG. 5.

Referring now to FIGS. 4 through 6, a second preferred alternative embodiment of the present invention is shown. This embodiment consists of a kit which can be used to be treat skin irritations of various sizes and shapes. The kit includes a medicated sheet 40 having a bibulous pad 42 as a first layer and an impermeable barrier 44 as a second layer. A thickened, topical anesthetic is imbibed in the bibulous pad. The bibulous pad 42 is similar to the bibulous pad discussed earlier except that it is much larger and is designed to be cut to a desired size by a user. The impermeable barrier may be a polymer sheet or other material which substantially blocks the passage of moisture therethrough. As in the earlier embodiments, other compounds may be imbibed in the bibulous pad along with the anesthetic.

The kit also includes an adhesive sheet 46 which comprises a sheet of thin material 48 with an adhesive coating 50 disposed thereon.

To use the kit, a user first cuts a piece of the medicated sheet 40 to the size and shape of the irritated region of the skin they wish to treat. The user then places the cut piece of the medicated sheet on the irritated region with the bibulous pad 42 contacting the skin. Finally, the user cuts a piece of the adhesive sheet 46 which is somewhat larger than the piece of the medicated sheet placed on the skin and uses the piece of the adhesive sheet to cover the piece of medicated sheet and affix the medicated sheet to the skin. An example of a resulting patch 52 is shown in FIG. 6. A piece of medicated sheet 54 has been cut to an irregular shape and has been covered by a somewhat larger piece of adhesive sheet 56.

Figure 7:
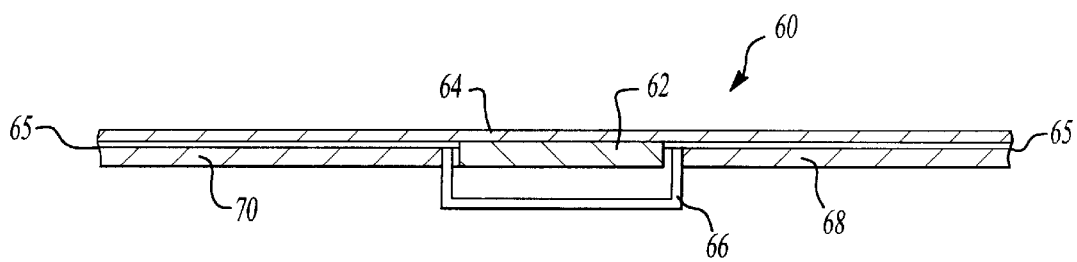
FIG. 7 is a cross-sectional side view of a medicated patch according to the present invention including an alternative embodiment of a release layer including a pad covering cup.

Referring now to FIG. 7, a medicated skin patch 60 is shown which is similar to the embodiment in FIG. 1. It includes a bibulous pad 62 and a sheet of thin material 64 which covers and extends beyond the pad 62. The thin material 64 has an adhesive coating 65 on one side. This embodiment utilizes a different release layer which includes a cup 66 which covers the side of the pad 62 not covered by the sheet of thin material 64. The cup 66 is at least semi-rigid and protects the pad 62 during shipping and storage. The cup 66 covers the pad 62 and leaves sufficient space to prevent medication imbibed in the pad 62 from being squeezed out of the pad during shipping and storage. Attached to the sides of the cup 66 and extending to cover the remainder of the patch 60 are two release sheets 68 and 70. When the user is ready to use the patch 60, they grip one of the release sheets 68 or 70 and remove the sheets 68 and 70 and the cup 66 from the patch. This exposes the medicated pad 62 and the adhesive layer 65.

In view of the teaching presented herein, other modifications and variations of the present inventions will be readily apparent to those of skill in the art. The foregoing drawings, discussion and description are illustrative of some embodiments of the present invention, but are not meant to be limitations on the practice thereof. It is the following claims, including all equivalents, which define the scope of the invention.

What is claimed is:

1. A medicated skin patch for delivering a topical anesthetic to a region of skin which has been irritated, the patch comprising:
   a bibulous pad for contacting and covering the irritated region;
   a thickened, topical anesthetic imbibed in the bibulous pad, said anesthetic comprising an active ingredient chosen from the group consisting of lidocaine, benzocaine, procaine, xylocaine, and combinations thereof; and
   a sheet of thin material covering the pad and projecting beyond the pad to form an attachment region, at least a portion of the attachment region having an adhesive coating disposed thereupon for fixing the sheet to the skin whereby the pad is held in contact with the irritated region.

2. The medicated skin patch according to claim 1, further comprising a topical antiseptic imbibed in the bibulous pad.

3. The medicated skin patch according to claim 2, wherein an active ingredient of the topical antiseptic is chosen from the group consisting of iodine, mercury, silver, a phenol, nitrofurazone, and combinations thereof.

4. The medicated skin patch according to claim 1, further comprising a topical antibiotic imbibed in the bibulous pad.

5. The medicated skin patch according to claim 1, further comprising an anti-inflammatory imbibed in the bibulous pad.

6. The medicated skin patch according to claim 5, wherein an active ingredient of the anti-inflammatory is chosen from the group consisting of aspirin and ibuprofen.

7. The medicated skin patch according to claim 1, further comprising an anti-irritant composition imbibed in the bibulous pad.

8. The medicated skin patch according to claim 7, wherein an active ingredient of the anti-irritant composition is chosen from the group consisting of antihistamines and calamine.

9. The medicated skin patch according to claim 1, further comprising a counter-irritant composition imbibed in the bibulous pad.

10. The medicated skin patch according to claim 9, wherein an active ingredient of the counter-irritant composition is chosen from the group consisting of capsaicin, menthol, and clove oil.

11. The medicated skin patch according to claim 1, further comprising a moisturizer imbibed in the bibulous pad.

12. The medicated skin patch according to claim 11, wherein the moisturizer is chosen from the group consisting of aloe, lanolin, glycerin, mineral oil, and combinations thereof.

13. The medicated skin patch according to claim 1, further comprising a release layer for covering the pad and the adhesive layer, the release layer being configured to be removed from the patch prior to affixing the patch to the skin.

14. The medicated skin patch according to claim 13, wherein the release layer comprises a first section and a second section, said second section overlapping a portion of said first section to form an overlapping portion so that said overlapping portion may be gripped for removing said second section from said patch.

15. The medicated skin patch according to claim 14, wherein said first section covers a portion of said attachment region and said second section covers said pad and a portion of said attachment region so that said overlapping portion is adjacent said attachment region.

16. The medicated skin patch according to claim 13, wherein the release layer includes a cup for covering said pad.

17. The medicated skin patch according to claim 1, wherein the sheet of thin material is a polymer sheet.

18. The medicated skin patch according to claim 17, wherein the attachment region of the thin material is perforated so that moisture from the skin adjacent the attachment region can penetrate the thin material.

19. The medicated skin patch according to claim 1, wherein the sheet of thin material is a woven material.

20. The medicated skin patch according to claim 17, further comprising an impermeable barrier between said pad and said woven material so that the anesthetic imbibed in said pad is prevented from penetrating said barrier.

21. A method for treating skin irritation due to an insect bite, the method comprising the steps of:
   a) providing a medicated skin patch for delivering a topical anesthetic to a region of skin which has been irritated, the patch comprising:
      a bibulous pad for contacting and covering the irritated region;
      a thickened, topical anesthetic imbibed in the bibulous pad; and
      a sheet of thin material covering and projecting beyond the pad to form an attachment region, at least a portion of the attachment region having an adhesive coating disposed thereon for affixing the sheet to the skin;
   b) placing the medicated skin patch on the skin so the pad contacts the irritated region; and
   c) affixing the attachment region of the patch to the skin to retain the pad in contact with the irritated region for a period of time.

22. A medicated skin patch kit for delivering a topical anesthetic to a region of skin which has been irritated, the kit comprising:

a medicated sheet having a first layer comprising a bibulous pad and a second layer comprising an impermeable barrier;

a thickened, topical anesthetic imbibed in the bibulous pad; and an adhesive sheet comprising a thin material and having an adhesive coating disposed thereon;

wherein a portion of said medicated sheet sufficient to cover the irritated region of skin can be cut from a remainder of said medicated sheet, a portion of said adhesive sheet sufficient to cover said portion of said medicated sheet and project there beyond can be cut from a remainder of said adhesive sheet; said portion of said medicated sheet can be placed on the irritated region so that said bibulous pad contacts the irritated region; and said portion of said adhesive sheet can be placed over said portion of said medicated sheet so that said adhesive coating faces the skin thereby affixing said portion of said medicated sheet and said portion of said adhesive sheet to the skin whereby the pad is held in contact with the irritated region.

* * * * *